US012410297B2

United States Patent
Toledo Antonio et al.

(10) Patent No.: US 12,410,297 B2
(45) Date of Patent: Sep. 9, 2025

(54) LIGNIN DEPOLYMERIZATION AND DEOXYGENATION PROCESS FOR OBTAINING AROMATIC COMPOUNDS AND THEIR CATALYTIC REACTION COMPOSITION

(71) Applicant: INSTITUTO MEXICANO DEL PETROLEO, Mexico City (MX)

(72) Inventors: Jose Antonio Toledo Antonio, Mexico City (MX); Maria Antonia Cortes Jacome, Mexico City (MX); Isidro Mejia Centeno, Mexico City (MX); Jorge Alberto Garcia Martinez, Mexico City (MX); Jose Escobar Aguilar, Mexico City (MX); Esteban Lopez Salinas, Mexico City (MX); Maria de Lourdes Araceli Mosqueira Mondragon, Mexico City (MX); Miguel Perez Luna, Mexico City (MX); Carlos Angeles Chavez, Mexico City (MX); Jaime Sanchez Valente, Mexico City (MX); Maria de Lourdes Alejandra Guzman Castillo, Mexico City (MX); Ana Karina Medina Mendoza, Mexico City (MX)

(73) Assignee: INSTITUTO MEXICANO DEL PETROLEO, Mexico City (MX)

(*) Notice: Subject to any disclaimer, the term of this patent is extended or adjusted under 35 U.S.C. 154(b) by 983 days.

(21) Appl. No.: 17/516,361

(22) Filed: Nov. 1, 2021

(65) Prior Publication Data

US 2022/0056236 A1    Feb. 24, 2022

Related U.S. Application Data

(62) Division of application No. 15/843,422, filed on Dec. 15, 2017, now Pat. No. 11,180,628.

(30) Foreign Application Priority Data

Dec. 15, 2016    (MX) .................. MX/a/2016/016674

(51) Int. Cl.
C08J 11/16          (2006.01)
B01J 20/32          (2006.01)
(Continued)

(52) U.S. Cl.
CPC ........... C08J 11/16 (2013.01); B01J 20/3204 (2013.01); B01J 21/04 (2013.01); B01J 23/74 (2013.01);
(Continued)

(58) Field of Classification Search
CPC ........ C08J 11/16; B01J 20/3204; B01J 21/04; B01J 23/74; B01J 23/75; B01J 23/755;
(Continued)

(56) References Cited

U.S. PATENT DOCUMENTS

| 2008/0050792 A1* | 2/2008 | Zmierczak | C10G 3/50 435/161 |
| 2013/0025191 A1* | 1/2013 | Chen | C10L 1/023 585/14 |
| 2016/0145497 A1* | 5/2016 | Lattner | C10G 3/50 585/323 |

* cited by examiner

Primary Examiner — David T Karst
(74) Attorney, Agent, or Firm — FisherBroyles, LLP; Jason P. Mueller (57) ABSTRACT

The present invention is related to a catalytic process, which includes catalytic compositions for depolymerisation and deoxygenation of lignin contained in the biomass for obtaining aromatic hydrocarbons. The catalytic composition includes at least one non-noble element from Group VIIIB of the periodic table supported on a mesoporous matrix composed of an inorganic oxide, which can be alumina surface-modified with a second inorganic oxide with the object of inhibiting the interaction between the active com- (Continued)

ponent and the support. The process of lignin depolymerisation includes dissolving lignin in a mixture of protic liquids, reacting it in a reaction system by batch or in continuous flow at inert and/or reducing atmosphere, at a temperature of between 60 to 320° C. and a pressure of from 5 to 90 kg/cm$^2$.

12 Claims, 2 Drawing Sheets

(51) Int. Cl.
| | |
|---|---|
| *B01J 21/04* | (2006.01) |
| *B01J 23/74* | (2006.01) |
| *B01J 23/75* | (2006.01) |
| *B01J 23/755* | (2006.01) |
| *B01J 29/03* | (2006.01) |
| *C07C 41/00* | (2006.01) |
| *C07C 45/52* | (2006.01) |
| *C07C 45/59* | (2006.01) |
| *C07C 47/58* | (2006.01) |
| *C07C 51/00* | (2006.01) |

(52) U.S. Cl.
CPC .............. *B01J 23/75* (2013.01); *B01J 23/755* (2013.01); *B01J 29/0333* (2013.01); *C07C 41/00* (2013.01); *C07C 45/52* (2013.01); *C07C 45/59* (2013.01); *C07C 47/58* (2013.01); *C07C 51/00* (2013.01)

(58) Field of Classification Search
CPC ...... B01J 29/0333; C07C 41/00; C07C 45/52; C07C 45/59; C07C 47/58; C07C 51/00; C07C 43/23; C07C 49/84; C07C 63/04
USPC .......................................................... 530/500
See application file for complete search history.

LIGNIN DEPOLYMERIZATION AND DEOXYGENATION PROCESS FOR OBTAINING AROMATIC COMPOUNDS AND THEIR CATALYTIC REACTION COMPOSITION

CROSS-REFERENCE TO RELATED APPLICATIONS

This patent application is a divisional of U.S. patent application Ser. No. 15/843,422, filed Dec. 15, 2017, which in turn claims priority under 35 U.S.C. § 119 to Mexican Patent Application MX/a/2016/016674, filed on Dec. 15, 2016, the disclosures of which are incorporated herein by reference in their entireties.

TECHNICAL FIELD OF THE INVENTION

The current invention is related to the catalytic process including catalytic reactions for the depolymerisation and deoxygenation of lignins contained in the biomass for obtaining aromatic hydrocarbons. The catalytic composition consists of at least one non-noble element from group VIIIB of the periodic table supported in a mesoporous matrix composed of an inorganic oxide, which can be alumina surface modified with a second inorganic oxide with the object of inhibiting the interaction between the active component and the support. The process of lignin depolymerisation consists of dissolving lignin in a mixture of protic liquids, react it in a batch reaction system or in a continuous flow reaction system at inert and/or reducing atmosphere, at a temperature consisting of between 60 to 320° C. and a pressure of between 5 to 90 Kg/cm². Oxygenated aromatic hydrocarbons are mostly produced when the reaction is developed in a batch system, while deoxygenated aromatic hydrocarbons are produced in a continuous flow reaction system.

BACKGROUND OF THE INVENTION

Human activity is the main cause of global warming and climate change. To carry out his domestic, transport and industrial activities man requires of energy, which he satisfies by the combustion of fossil fuels and which generates great amounts of greenhouse effect gases. However, said activities that are associated with the emission of gases are essential for the world economy and form a fundamental part of modern life; therefore, there must exist a suitable balance between the growing energy demand and the urgent need to protect the environment and climate. Reason for which, there is the need to develop viable and sustainable novel energy sources, such as biorefinary technologies, which maximize the yield of renewable fuels, biological origin chemical products, and bioenergy. In fact, there have surged program policies and national plans in Europe as well as the United States of America, to develop bio-energy. The results indicate that the conversion of biomass to biofuels can give origin to a renewable and sustainable energy source for obtaining liquid fuels for transport.

Recent studies suggest that only in the United States of America 1.3 billion tons of biomass can be produced annually in a sustainable manner from agriculture and forestry. Which indicates that it can provide biomass as a raw material sufficiently to substitute at least 30% of the liquid fuels needs for transport in the U.S.A., without compromising its food production needs, by the suitable coupling of advanced technologies for the transformation of biomass with the changes in soil use. Even when the production of biofuels must yet overcome multiple technical and economical challenges, various cellulosic ethanol plants have been projected at a commercial level.

In first generation cellulosic bioethanol plants, great amounts of lignin will be produced as a by-product, from grains. This lignin is underutilized since about 60% more of it is produced than the amount required to satisfy the internal energy requirements of the plant by its combustion. Lignin is considered an affordable renewable source and of potential industrial use, whose annual production has been estimated to be in the range of $5\text{-}36\times10^8$ annual tonnes worldwide. It is considered the second most abundant compound on Earth, after cellulose and its structure is composed mainly of phenylpropanoid units, which makes it the only renewable source of great volume composed mainly of aromatic hydrocarbons. Therefore, it is important to develop new processes for its transformation into chemical products of greater added value. Moreover, the department of energy of the United States of America has projected obtaining 79 billion litres per annum of second generation bioethanol (from agroindustrial residues) starting on 2022, for which about 223 million tons of biomass will be used annually and will produce about 62 million tons of lignin annually. Lignin produced as so will exceed by far the current needs of lignin in the world market for obtaining speciality products.

On the other hand, lignocellulosic materials coming mainly from agroindustrial residues contain between 15 and 30% lignin. Lignin is found forming an organic biopolymer, which envelops holocellulose (cellulose+hemicellulose). In order to take advantage of and convert cellulose and hemicellulose contained in the biomass to glucose and xylose, pentose and hexose, and subsequently to ethanol, it is necessary to extract the lignin contained in the biomass. Lignin contained in the biomass consists of an amorphous polymer containing in its structure great amounts of phenylpropanoid compounds, aromatic groups and methoxide groups and OH's, which must be used up for their transformation into chemical compounds of higher added value such as a renewable source to obtain aromatic hydrocarbons such as BTX fraction, vanillin, guaiacol, cresols, etc.

Lignin is an abundant source of renewable raw materials, being the future applications and perspectives very promising. However, although great amounts of lignin are produced, about 98% of this material is burnt directly into the same manufacturers in an energy recovery stage. Only 2% is commercially exploited. It seems that during the next few years this will be a promising field for obtaining chemical products with high added value. Thus, lignin represents a renewable and potentially valuable source for obtaining chemical compounds mainly of the aromatic type. Therefore, it represents an opportunity to develop chemical and biological processes for the degradation of the biopolymer, which could be used both for holocellulose decomposition and the production of biofuels, as well as to generate aromatic chemical products from lignin. And so, form the basis of a "bio-refinery".

Lignin is a heterogeneous mixture of aromatic polymers, which are rigid and resistant, and serve to protect the polysaccharides in the cell walls from degradation and chemical attacks. The content of lignin in the biomass varies depending on the origin of the biomass: soft woods have between 25-35% weight, while the herbaceous biomass contains between 14-20% weight. The most important challenge to give value to lignin resides in selectively breaking the C—O linkages to produce simpler aromatic compounds, appropriate to integrate into petrols, to be used as chemicals per se or as precursors for their transformation into products of higher added value. Although the advances in the conversion of lignin into high added value chemicals and biofuels, its combustion to generate energy is still favoured and, commercially, is its only viable use, until today. Therefore, the object of this patent is to establish a catalytic process, which allows transforming lignins and agroindustrial residues, lingo-cellulosic renewable sources, into chemical products of high added value, maximizing the yield to aromatic compounds and phenols.

BRIEF DESCRIPTION OF THE FIGURES

With the purpose of having an understanding of the lignin depolymerisation and deoxygenation process for obtaining aromatic compounds and its catalytic reaction composition, objects of the present invention, reference will be made to the accompanying figures, without limiting its scope.

DETAILED DESCRIPTION OF THE INVENTION

This invention is related to a catalytic process, which includes catalytic compositions for the depolymerisation of lignins contained in the biomass for obtaining aromatic hydrocarbons. The process consists of submitting lignin to a hydrothermal and/or solvothermal treatment in a protic liquid, with or without a catalyst with the object of solubilizing lignin, eliminating inorganic solids and solid impurities contained therein, and depolymerising or partially fragmenting lignin into its different monoaromatic units. Partially depolymerised lignin soluble in a protic liquid is obtained from this process, which afterwards passes through a fixed bed reactor packed with a catalytic composition, also object of the present invention, to obtain a mixture of oxygenated and/or partially deoxygenated aromatic compounds contained in the protic solvent.

The catalytic compositions, object of the present invention, consist of a mixed oxide, which can contain alumina and/or silica and can contain or not, at least one non-noble metal element of the VIIIB group of the periodic table deposited in its surface, to increase the density of active sites for the hydrotreating and hydrodecarboxylation reactions, specifically hydrodeoxygenation or decarboxylation of the oxygenated aromatic hydrocarbons produced during depolymerisation.

Therefore, the present invention provides an aluminium oxide material which serves as a catalyst and/or alumina support from a boehmite-phase precursor, which is formulated in cylindrical, trilobal or tetralobular extrudes with resistance to fracture superior to 3 lbf/mm by the addition of a solution containing an organic or inorganic acid to formulate the paste with suitable consistency to be extruded. Once the extrudes are obtained, they are dried and burnt at temperatures higher to 400° C. to obtain the support in alumina-phase extrudes. The obtained extruded is subjected to a surface modification process consisting of the impregnation of an inorganic oxide with a concentration of less than or equal to 15% by weight and it is subsequently burnt at a temperature of over 400° C., thereby obtaining a support and/or catalyst with surface characteristics and acid properties suitable for the lignin depolymerisation reaction and for preparing catalysts containing at least one non-noble metal component of the VIIIB group of the periodic table as active phase for the lignin depolymerisation and deoxygenation process.

In this regard, it is worth pointing out that the obtained aluminium oxide material has improved textural properties by increasing the diameter and volume of the pore, which serve as catalyst and/or alumina-based catalyst support obtained from an aluminium oxyhydroxide precursor, preferably of bohemite phase, which peptizes with an inorganic acid, reacting the aluminium oxyhydroxide with an aqueous solution containing an inorganic acid at a molar concentration of 0.01 to 1 M; subsequently, the peptized oxyhydroxide material is reorganised around a surfactant of high volume, preferably of neutral character, by the addition of said surfactant to the solution. During this process, the aluminium oxyhydroxide nanoparticles are peptized and partially dissolved. Afterwards, it is left to cool at a temperature of between 2° and 40° C. and a neutral surfactant is added, a three-block type copolymer forming micelles in the solution, around which the peptized aluminium oxyhydroxide nanoparticles are reorganized and it is left stirring for 4 to 36 hours. A surfactant/aluminium oxyhydroxide ratio was used comprising from 0.1 to 10. Finally, the material is dried at a temperature of between 5° and 120° C. for a time of between 12 and 72 hours. Subsequently, the surfactant is removed from the obtained material by burning at air atmosphere, passing an air flow comprising from 20 to 100 $cm^3$/minute for 4 to 12 hours. The resulting solid is subjected to a surface modification process consisting of the impregnation of an inorganic oxide at a concentration of less than or equal to 15% by weight and its subsequent burning at a temperature of over 400° C., thereby obtaining a support and/or catalyst with surface features and acid properties suitable for the lignin depolymerisation reaction and for preparing catalysts containing at least one non-noble metal component of the VIIIB group of the periodic table as active phase for the process of lignin depolymerisation and deoxygenation.

The mesoporous alumina support with pore diameters superior to 15 nm can be subjected to a process of extraction before or after its surface modification with inorganic oxide, by the addition of a solution containing an organic or inorganic acid to formulate the paste with suitable consistency to be extruded. The obtained paste is formulated in cylindrical, trilobal or tetralobular extruded. Once the extruded are obtained, they are dried and burnt at temperatures higher than 400° C. to obtain the support in alumina-phase extruded or surface-modified alumina with inorganic oxide. If the obtained extruded has not been surface modified with an inorganic oxide, it is subjected to a surface modification process consisting of the impregnation of an inorganic oxide at a concentration of less than or equal to 15% by weight and its subsequent burning at a temperature above 400° C., thereby obtaining a support and/or catalyst with surface features and suitable acid properties for the lignin depolymerisation reaction and for the preparation of catalysts containing at least one non-noble metal component of the VIIIB group of the periodic table as active phase for the lignin depolymerisation and deoxygenation process.

An object of the present invention is to obtain active catalysts for lignin depolymerisation and hydrodeoxygenation by impregnation in incipient wet of at least one non-noble metal component of the VIIIB group of the periodic table, which consists in dissolving a precursor salt of the metal element in a protic solvent at such a concentration which allows obtaining a concentration comprised between 2 and 20% by weight of the metal element in the final solid. The metal component of the VIIIB group of the periodic table can be nickel, cobalt or iron, and the precursor salt of said metal component can be chlorine, nitrate, acetate, carbonate or hydroxycarbonate, etc. and the protic liquid can be water or any alcohol such as methanol, ethanol, 1-propanol or isopropanol, 1-butanol, etc.

The impregnation method by incipient wet consists of contacting the solution containing the precursor salt of the metal element of the VIIIB group of the periodic table with the formulated support in cylindrical, trilobal or tetralobular extruded, modified with an inorganic oxide and previously dried in an oven at 110° C., until all the solution is absorbed by filling in the volume of pores of said support. Afterwards, it is left standing keeping the surface of the support wet with said solution for a period of time of 12 to 18 hours. Subsequently, it is dried at 110° C. and it is burnt at a temperature comprised between 40° and 600° C. in air atmosphere, passing air fluid comprising between 20 to 100 $cm^3$/minute for 4 to 12 hours.

An embodiment of the process of the present invention is the lignin thermal and/or catalytic depolymerisation process by a liquid reformation process with a protic solvent or mixture of solvents in a reactor by autoclave-type batches. Said process consists of dissolving lignin in a mixture of protic solvents, basically in alcohol-water at a ratio comprised of 10:90 to 90:10 vol: vol, when lignin is soluble in protic solvents, or when lignin is insoluble, the insoluble solid is added to the mixture of protic solvents and the temperature is increased to dissolve and reach the reaction temperature. Soluble or insoluble commercial lignin can be used as a lignin source, such as sodium lignosulfonate, alkaline Kraft lignin, organosolv lignin, lignin obtained from any lignocellulosic residue as a cellulose and hemicellulose hydrolysis by-product in order to produce alcohols, and/or residue waste by-products named "black liqueur" of the paper industry, and/or the same biomass or lignocellulosic agroindustrial residue rich in lignin, such as wood chip, sugar cane bagasse, agave bagasse, etc. The alcohol used as protic solvent can be any primary or secondary alcohol, such as methanol, ethanol, propanol, isopropanol, 1-butanol, 2-butanol etc., preferably methanol or ethanol. The amount of lignin or black liqueur or biomass as lignocellulosic residue is between 10 to 250 g/L, preferably from 10 to 150 g/L. To carry out a thermal reaction the solution containing lignin is loaded onto an autoclave, sealed tightly, a test for leakages is carried out and the oxygen present is removed by nitrogen scanning twice and the stirring is started at 250 rpm. Afterwards, the heating is started with a ramp of from 1 to 10° C./min until reaching the reaction temperature of between 80 to 300° C. Once the reaction temperature is reached, the pressure is configured with an inert gas or with a reducing gas until reaching a pressure in the system of between 30 and 90 kg/$cm^2$. Finally, it is left to react for a reaction time of between 0.5 to 4 hours, preferably of between 0.3 and 2 hours.

Once the reaction period is finished, the liquid containing the depolymerised lignin is filtered to remove non-transformed solids, solid residues and/or catalyst. Afterwards, the separation process of the depolymerised organic compounds containing mainly aromatic compounds is carried out by the addition of an aprotic polar solvent and vigorous stirring of the resulting liquid, with which the separation of two phases is carried out. The liquid is placed in a separation funnel by which an organic fraction and an aqueous fraction are separated. In the organic fraction, the resulting aromatic organic compounds are dragged from the lignin depolymerisation, which can contain both oxygenated and deoxygenated aromatic compounds, and other organic compounds such as alcohols, ketones, naphthenes, olefins, paraffin, carboxylates, carboxylic acids, etc. and in the aqueous fraction, dissolved non-reacted lignin is mainly found, small quantities of hydrocarbons which were not extracted with the aprotic polar solvent, inorganic salts contained in the lignin of origin.

Figure 1:
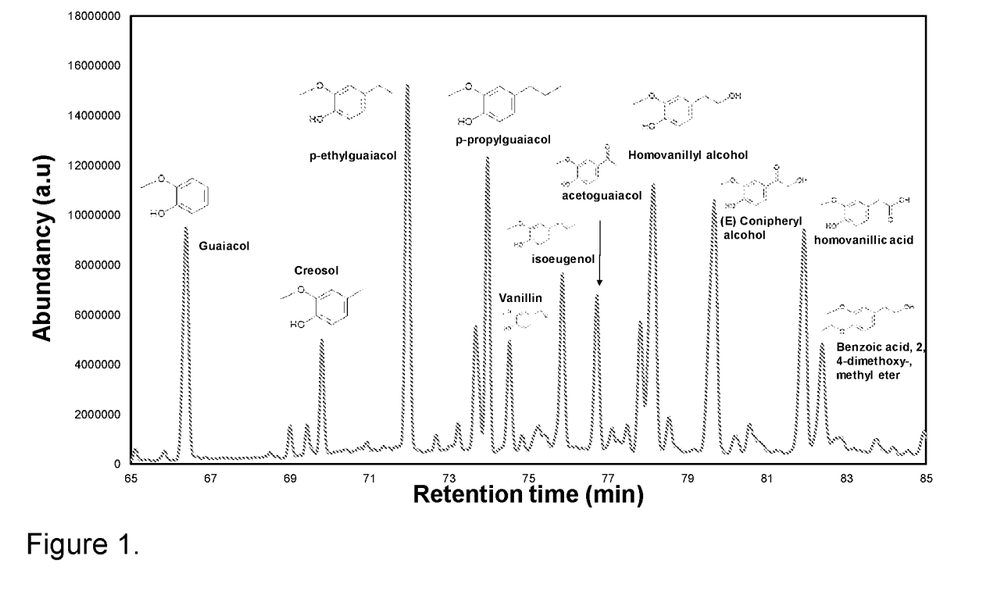
FIG. 1 shows an illustrative chromatogram of the different products obtained after the lignin depolymerisation reaction.

The aprotic polar solvent, which is used for the recovery of the organic compounds of the reaction products coming from the reactor by autoclave-type batches, can be selected from tetrahydrofuran or dichloromethane, preferably dichloromethane, since it shows a lower boiling temperature, of about 40° C. Once the organic fraction is separated it is subjected to a distillation process at the boiling temperature of the aprotic polar solvent with the object of recovering the solvent used for the extraction of the organic compounds, and afterwards it is distilled at the temperature of the alcohol used for the reaction with the object of removing the alcohol fraction which is dragged in the aprotic polar solvent, said temperature is from between 6° and 100° C. The resulting liquid product of the reaction was analysed in a gas chromatograph coupled to a mass spectrometer, with which the identification of the different compounds present was carried out. FIG. 1 shows an illustrative chromatogram of the different products obtained after the lignin depolymerisation reaction. The aqueous fraction is distilled at a temperature of 100° C., in order to remove all water and thereby recover the dissolved solid, with the object of determining the percentage weight of lignin converted into products. The selectivity is determined by considering the area below the curve of each chromatographic peak identified with a probability assignment greater than 80, and the peaks not identified with said probability were grouped as non-identified compounds.

Another embodiment of the process of the present invention is the realization of the lignin thermal and/or catalytic depolymerisation reaction by a process in continuous flow, which consists of a pre-treatment section of the feeding load which at the same time consists of the lignin dissolution in a mixture of protic solvents, basically in alcohol-water at a ratio comprising 10:90 to 90:10 vol: vol, when the lignin is soluble in protic solvents, afterwards and with object of removing all cations and anions of the inorganic compounds present in lignin, said components are contacted with cationic and anionic interchange resins consecutively, with which inorganic cations are removed such as sodium, potassium, calcium, silicon, etc., and anions such as sulphates, nitrates, chlorides, etc. Once the inorganic cations and anions are removed, the lignin solution is pumped to a reactor wherein it is contacted with the catalyst, in the case of the reaction being catalytic; and for the thermal reaction the reactor is packed with silicon carbide and therefore the lignin solution is contacted with the silicon carbide.

The process in continuous flow consists of a reaction section composed of a tubular reactor packed with an inert material when the reaction is carried out by a thermal reaction or with a catalyst, in the case of the reaction being carried out with a catalyst. The catalyst and/or silicon carbide are loaded onto the reactor with a granulometry comprising from 200 microns up to 2.0 mm, be it mechanically grinded or directly into cylindrical, trilobal or tetralobular extruded. Before feeding the reacting lignin solution, the catalyst is activated by a reduction process, which consists of heating the reactor in presence of a reducing gas at high pressure. The reactor is heated at a temperature of between 300 to 500° C., with a reducing gas flow, preferably hydrogen of 3 to 8 L/hour maintaining a pressure in the reactor of between 30 to 90 kg/cm$^2$. Once the catalyst is activated, the solution containing the resulting lignin is passed through the reactor at a flow speed comprising between 5 and 50 mL/hour, in order to maintain the spatial temperature of the liquid with regards to the catalyst volume (LHSV, liquid hourly space velocity) comprised of between 0.5 and 10 hr$^{-1}$. The lignin depolymerisation reaction can be carried out with inert gas flow or with a gas or reducing agent. When it is carried out with inert gas flow, an inert gas is passed which can be nitrogen, helium, argon, and/or a mixture thereof at a flow speed comprising between 1 and 10 L/h, keeping a pressure comprising between 30 and 90 kg/cm$^2$. When the reaction is developed with a reducing agent, a hydrogen flow is passed at a flow speed comprising between 1 and 10 L/h, keeping a pressure of between 2 and 30 kg/cm$^2$.

The recovery of the reaction products is carried out in a condenser placed on the outlet of the reactor wherein the liquid effluents are condensed at room temperature, and it is separated from the gases generated during the reaction. The generated gases are analysed by a gas chromatograph connected in line and the liquid effluents are recovered for their subsequent treatment and analysis to identify the reaction products.

When the reaction is carried out with inert gas, the products identified in the reaction gases are hydrogen, carbon monoxide, carbon dioxide, oxygen and $C_1$-$C_6$ hydrocarbons, paraffin, isoparaffin, olefins, isooleffins, etc. When the reaction is carried out in hydrogen flow, the reaction gases are composed mainly of carbon dioxide, carbon monoxide, $C_1$-$C_6$ hydrocarbons, paraffin, isoparaffin, olefins, isooleffins, etc.

The resulting liquid products of the reaction consist of a crystalline solution slightly yellow transparent, which is indicative of it not containing non-transformed lignin and that lignin has been depolymerised into simpler chemical compounds. When lignin is found without transformation, it generally consists of a black colour dark solution; in fact, the lignin solution fed to the system consists of a black colour dark solution, and the reaction product derived therefrom is transparent of clear yellow colour.

Figure 2:
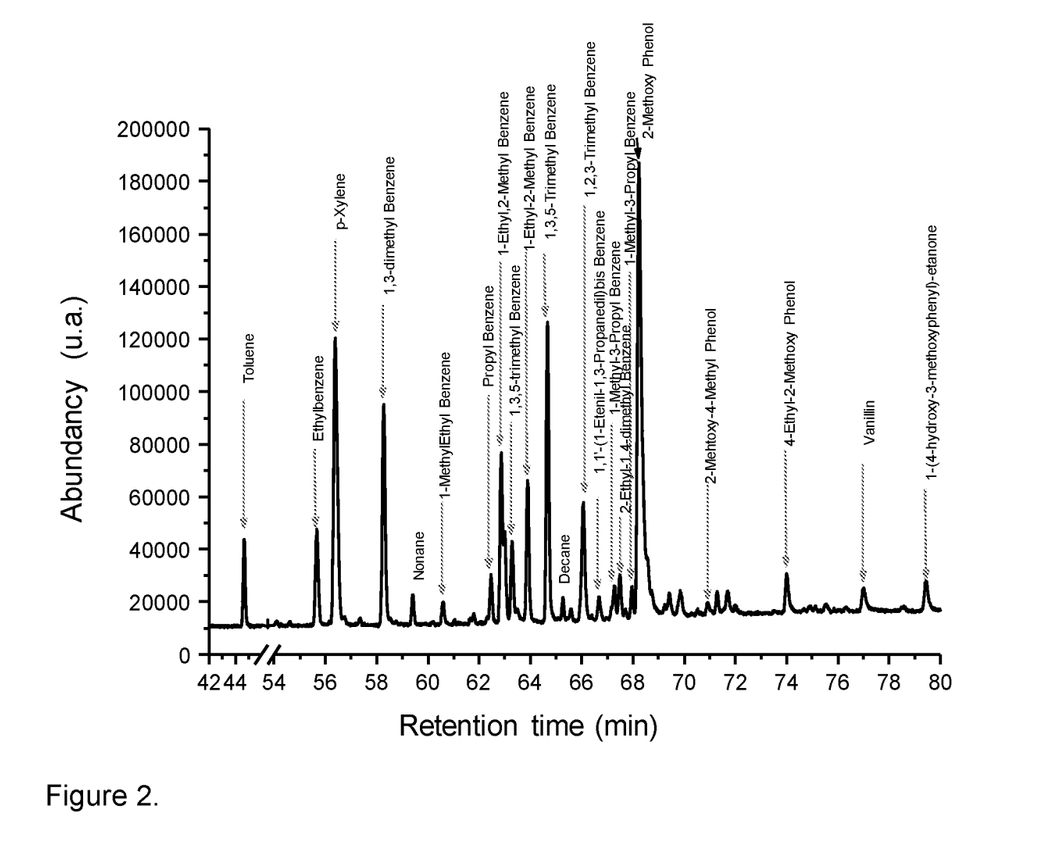
FIG. 2 shows an illustrative chromatogram of the different products obtained after the lignin depolymerisation and deoxygenation reaction.

The liquid fraction containing the reaction products is subjected to a separation procedure of the depolymerised organic compounds, which mainly contain aromatic compounds, by the addition of an aprotic polar solvent and a vigorous stirring of the resulting liquid, with which the two-phases separation is carried out. The liquid is placed in a separation funnel by which an organic fraction and an aqueous fraction are separated. In the organic fraction the resulting aromatic organic compounds are dragged from the lignin depolymerisation, which can contain both oxygenated and deoxygenated aromatic compounds, and other organic compounds such as alcohols, ketones, naphthenes, olefins, paraffin, carboxylates, carboxylic acids, etc., and in the aqueous fraction, non-reacted lignin is mainly found dissolved, small amounts of hydrocarbons which were not extracted with the aprotic polar solvent, inorganic salts contained in the lignin of origin. When the total conversion of lignin is reached, the aqueous fraction resulting from the separation is crystalline, transparent and colourless, indicating that there is no lignin dissolved therein. For the recovery of reaction products in the continuous flow process, an extraction treatment with an aprotic polar solvent is carried out in the same manner as for the reaction products of the reactor by autoclave-type batches, for the separation of organic compounds from the aqueous fraction, as described above. FIG. 2 shows an illustrative chromatogram of the different products obtained after the lignin depolymerisation and deoxygenation reaction in a fixed bed and continuous flow reactor.

Now we mention some of the compounds obtained by the process of the present invention under its two embodiments, but that are in no way exclusively limited thereto: a) identified non oxygenated aromatic compounds are: toluene, ethyl benzene, para-xylene, meta-xylene and ortho-xylene, trimethyl-benzene, ethyl-methyl benzene, propyl-ethyl benzene, generally di- and trialkyl-benzenes; b) oxygenated aromatic compounds are: phenol, 2-metoxyphenol, 4-methyl-2-metoxyphenol, 2,6-dimetoxyphenol, 1,2-dimetoxybenzene, 4-ethyl-2-metoxyphenol, 4-propyl-2-metoxyphenol, etc.

REFERENCES

[1] A. P.C. Faaij. Energy policy 34 (2006) 322-342;
[2] U.S. Department of Energy, Office of the Biomass Program (OBP), Biomass Multi-Year Program Plan (2014): http://www1.eere.energy.gov/bioenergy/pdfs/mypp april_2011.pdf;
[3] European Biofules Technology platform, 6th Stakeholder Plenary Meeting SPM6, 14-15 Oct. 2014 Brussel, Belgium http://www.biofuelstp.eu/spm6/spm6.html.
[4] A.V. Bridgwater, Review of fast pyrolysis of biomass and product upgrading Biomass and Bioenergy, Volume 38, March 2012, Pages 68-94;
[5] X. Cai, X. Zhang and D. Wang. Environ. Sci. Technol. 45 (2011) 334-339;
[6] U.S. Department of Energy. 2011. U.S. Billion-Ton Update: Biomass Supply for a Bioenergy and Bioproducts Industry. R.D. Perlack and B.J. Stokes (Leads), ORNL/TM-2011/224. Oak Ridge National Laboratory, Oak Ridge, TN. 227p. http://www1.eere.energy.gov/bioenergy/pdfs/billion ton update.pdf;
[7] M. E. Himmel et al., Biomass recalcitrance: Engineering plants and enzymes for biofuels production. Science 315, 804-807 (2007). doi: 10.1126/science. 1137016;
[8] http://energy.gov/eere/bioenergy/processing-and-conversion (2015);
[9] B. E. Dale, R. G. Ong, Energy, wealth, and human development: Why and how biomass pretreatment research must improve. Biotechnol. Prog. 28, 893-898 (2012). doi: 10.1002/btpr. 1575;
[11] Goran Gellerstedt and Gunnar Henriksson, Monomers, Polymers and Composites from Renewable Resources Lignins: Cap 9, Major Sources, Structure and Properties, 201-224 (2008).
[12] M. Kleinert, T. Barth, Towards a lignocellulosic biorefinery: Direct one-step conversion of lignin to hydrogen-enriched biofuel. Energy Fuels 22, 1371-1379 (2008).

EXAMPLES

Now the invention will be further described by reference to examples related to the lignin depolymerisation and deoxygenation process for obtaining aromatic compounds and their catalytic reaction composition, objects of the present invention and previously described, without them limiting the scope of the present invention.

Thermal and catalytic depolymerisation experiments on lignin Kraft were carried out in ethanol-water at temperatures of 60 to 290° C., at a pressure of 2,413 to 8,274 kPa (350 to 1200 psi), and lignin/solvent ratios (ethanol+water) of 2 to 20 g/L.

EXAMPLE 1. Preparation of Cylindrical Particles (Extruded) Gamma-Alumina Phase (EA). Supports of gamma-Al2O3 formulated in the form of cylindrical particles were obtained from an alumina-hydrated precursor (commercial bohemite), for which the bohemite powder material is dried at 110° C. for 20 hours, it is sifted using a mesh EE.UU. 100, with an opening of 0.149 mm, to homogenize the particle size. In order to formulate the extruded, 500 g of powdered material bohemite phase was used, which was placed on a mixer (Bench Kneader, Mod. PNV-1) slowly adding 100 ml of a $HNO_3/H_2O$ solution at 1% mol, for a period of 2.5 hours, without interrupting the mixing, by which a moist paste of bohemite is formed of uniform consistency and malleable at the same time, this paste was introduced into an extruder (DOTCO, Mod. BA-293), using compressed air at a pressure of 1,100 kPa; the obtained extruded had cylindrical and trilobal form of 1/16" diameter. Said extruded were left standing at room temperature (25° C.) for a period of time of between 18 and 24 hours; afterwards, they were subjected to a drying process on a convection oven, firstly at a temperature of 60° C. for 4 hours, afterwards the temperature was increased to 80° C. for 5 hours, and lastly the temperature was increased to 120° C. for 16 hours. For the burning of the extruded, a heating ramp was used of 5° C./min up to 550° C. staying at these conditions for 4 hours under air flux of 150 mL/min. The X ray analysis shows that the crystalline phase of the extruded obtained after the burning corresponds to the gamma-alumina. The textural properties of this support (SAS) showed a specific area of 300 $m^2/g$, pore volume of 0.74 $cm^3/g$ and average pore diameter of 9.9 nm.

EXAMPLE 2. Preparation of cylindrical particles (extruded) gamma-alumina phase modified with silica according to the invention (EAS). In order to prepare the EAS support, the EA support prepared in Example 1 was used. The EA support in the form of previously burnt extruded, was dried in the oven at 120° C. for two hours, afterwards it was modified with 5% by weight of $SiO_2$ by the following procedure:

In a 3 L flask anhydrous ethanol is mixed with tetra-ethyl-orthosilicate (TEOS, $SiC_8H_2OO_4$), using magnetic stirring. Afterwards, the temperature in the flask is increased up to 70° C. and it is maintained at reflux for 1 hour. Then, it is cooled at 25° C. When this temperature is reached, the hydrolysis of the TEOS is used using slow drop-by-drop of a mixture of anhydrous ethanol, water and nitric acid, with a molar ratio of $H_2O$/TEOS=4, ethanol/TEOS=40 y $HNO_3$/TEOS=0.1.

After adding the hydrolysis solution, it is left stirring for 30 minutes at room temperature (25° C.). Afterwards, the alumina support extruded previously dried in an oven at 120° C. are added and it is left standing for 12 hours at room temperature. Then, the filtration of the TEOS-modified support is carried out and the extruded are dried at 120° C. for a period of 18 hours. Finally, the extruded are burnt in air flow at 400° C. for 18 hours. The final composition of the extruded support gamma-alumina phase modified with silica was: O=48.39% by weight, AL=48.06% by weight and Si=3.55% by weight, and its textural properties show an specific area of 275 $m^2/g$, pore volume of 0.61 $cm^3/g$ and pore diameter of 8.9 nm.

EXAMPLE 3. Preparation of cylindrical particles (extruded) mesoporous gamma-alumina phase (EAS Meso). 12 g of pseudobohemite were peptized (AlOOH) with a nitric acid solution 0.334 M. To the obtained suspension, Pluronics P-123 surfactant was added and was left shaking for 24 hours at room temperature. A surfactant/AlOOH (w/w) ratio=2, was used. Afterwards, the obtained mixture was dried at 50° C. for 24 hours and afterwards at 90° C. for 24 hours; finally, the obtained material was thermally treated with air flow of 100 mL/min to remove surfactant, using a ramp of 1° C./min up to 300° C./min for 4 hours and afterwards from 1° C./min up to 500° C. for 6 hours.

Afterwards, the material was meshed above 100 mesh (<160 µm) and dried at 110° C., and for its moist extrusion, the powder was mixed with a citric acid solution at 1% by weight. The paste was formulated in cylindrical extruded of a 1/16" diameter, first drying at room temperature for 24 hours; and then drying at 60° C. for 4 hours, 80° C. for 5 hours and at 100° C. for 12 hours. Immediately, it was thermally treated at 1° C./min up to 500° C. for 6 hours in air flow using air flow at 150 mL/min.

Subsequently, silica is added (via TEOS) to obtain the extruded (5% weight of $SiO_2$) by the procedure used in Example 3.

EXAMPLE 4. Preparation of the zeolite phase material (MMZ-112C, MMZ-113C and MMZ-114C). The preparation of zeolites was carried out as described in the patents (MX320407, EP 2 570 386 B1). The materials MMZ-112C, MMZ-113C, MMZ-114C, were prepared by the depolymerisation method at 200, 225 and 180° C., respectively. In all cases the recrystallization was carried out at a temperature of 150° C. and were burnt at 550° C. for a period of 6 hours.

EXAMPLE 5. Preparation of cylindrical particles (extruded) extruded material alumina-silica-zeolite phase (ExMMZ-112C). To 5.79 g of EAS, 5.2 mL of 5% $HNO_3$/$H_2O$ were added until having a moist paste, afterwards 5.4 mL of $H_2O$ were added. To this paste 15 g of MMZ-112C+16 mL $H_2O$, were added. 0.55 g of Ludox-TMA and 0.5 g of ethyl-methyl-cellulose (EMC, Dow Corning) were added in the form of gel adding with 1.9 mL water. The resulting moist paste was stable for extrusion. This material in the form of cylindrical extruded presents an specific area (Langmuir) of 652 $m^2/g$, an specific area (microporous) of 543 $m^2/g$, total pore average volume of 0.399 $cm^3/g$ and a pore diameter of 15.57 (Å).

EXAMPLE 6. Preparation of cylindrical particles (extruded) extruded material alumina-silica-zeolite phase (ExMMZ-113C). First, 0.513 g of ethyl-methyl-cellulose (EMC, DowCorning) were gelled with 2.9 mL of 5% volume $HNO_3/H_2O$, and afterwards 10.5 g of EAS in powder+15.9 mL of 5% volume $HNO_3/H_2O$, were added. Once the moist paste was formed, 4.5 g of MMZ-113C were added to obtain a lumpy mixture. Moreover, 2.0 mL of deionized water were added to for a malleable and stable paste. The extrusion was carried out using a diameter of 1/16". This material in the form of cylindrical particles presents a specific area (Langmuir) of 464 $m^2/g$, a specific area (microporous) of 237 $m^2/g$, total pore average volume of 0.62 $cm^3/g$ and pore diameter of 73 (Å).

EXAMPLE 7. Preparation of cylindrical particles (extruded) extruded material alumina-silica-zeolite phase (ExMMZ-114C). First, 0.503 g of ethyl-methyl-cellulose (EMC, DowCorning) were gelled with 3.0 mL 5% volume $HNO_3/H_2O$, and 10.5 g of EAS in powder+16.5 mL of 5% volume $HNO_3/H_2O$ were added afterwards. Once the paste was formed, 4.5 g of MMZ-114C were added to again have a lumpy mixture. 2.0 mL of deionized water were added additionally to forma malleable and stable paste. The extrusion was carried out with a diameter of 1/16". This material in the form of cylindrical particles presents a specific area (Langmuir) of 536 $m^2/g$, a specific area (microporous) of 327 $m^2/g$, total pore average volume of 0.75 $cm^3/g$ and pore diameter of 77 (Å).

EXAMPLE 8. Preparation of catalyst 15Ni-EAS. The impregnation solution was prepared by dissolving 10.3 g of nickel nitrate $Ni(NO_3)_2 \cdot 6H_2O$, in 77.6 ml of water double-distilled with stirring. Once the nickel was dissolved the solution turned transparent green. Afterwards, the solution was concentrated to a suitable volume to be used in the impregnation of 17.65 g of support EAS to fill in the pores. The amount dissolved salts varies based on the metal concentration desired to be obtained in the final solid which was of 15% weight nickel, the material was taken to a drying process at 120° C. for a period of 12 hours and afterwards the burning in air flow at a temperature of 400° C. for 4 hours. The catalyst was labelled as 15Ni-EAS.

EXAMPLE 9. Preparation of the catalyst 15Co-EAS. The impregnation solution was prepared by dissolving 8.8 g of cobalt acetate $C_4H_6CoO_4 \cdot 4H_2O$, in 25 mL water double distilled with stirring. Once the cobalt was dissolved, the solution turned wine red. Afterwards, the solution was concentrated at a suitable volume to be used in the impregnation of the EAS support to fill in pores. The amount of salts dissolved varies based on the concentration of metals desired to be obtained in the final solid, which was of 15% by weight of cobalt, the material was taken to a drying process at 120° C. for a period of 12 hours and afterwards to the burning in air flow at a temperature of 400° C. for 4 hours. The catalyst was labelled as 15Co-EAS.

EXAMPLE 10. Preparation of the catalyst 15Ni-EASMeso. The impregnation solution was prepared by dissolving 10.3 g of nickel nitrate $Ni(NO_3)_2 \cdot 6H_2O$, in 77.6 ml of water double-distilled with stirring. Once the nickel was dissolved the solution turned transparent green. Afterwards, the solution was concentrated up to a suitable volume to be used in the impregnation of 17.65 g of support EAS by filling in pores. The amount of dissolving salts varies based on the concentration of metals desired to be obtained in the final solid which was of 15% by weight of nickel, the material was taken to a drying process at 120° C. for 12 hours, and afterwards a burning in air flow at a temperature of 400° C. for 4 hours. The catalyst was labelled as 15Ni-EASMeso.

EXAMPLE 11. Preparation of catalyst 15Ni-ExMMZ-112C. The impregnation solution was prepared dissolving 8.75 g of nickel nitrate $Ni(NO_3)_2 \cdot 6H_2O$ in 66 mL of water double-distilled with stirring. Once the nickel was dissolved, the solution turned transparent green. Afterwards, the solution is concentrated at a suitable volume to be used in the impregnation of 13.2 g of support ExMMZ-112C to fill in pores. The amount of dissolved salts varies based on the concentration of metals desired to be obtained in the final solid which was of 15% by weight of nickel; the material was taken to a drying process at 120° C. for a period of 12 hours and afterwards the burning in air flux at a temperature of 400° C. for 4 hours. The catalyst was labelled as 15Ni-ExMMZ-112C.

Table 1 shows all catalysts prepared with metal and without metal, objects of the present invention as well.

TABLE 1

Preparation of supports and catalysts.

| Catalyst | Support | Metal (% weight) Ni | Co | Example |
|---|---|---|---|---|
| EA | $Al_2O_3$ | — | — | 1 |
| EAS | $Al_2O_3$—Si | — | — | 2 |
| EASMeso | $Al_2O_3$ mesoporous-i | | | 3 |
| MMZ-112C | Zeolite mesoporous | | — | 4 |
| MMZ-113C | Zeolite mesoporous | | | 4 |
| MMZ-114C | Zeolite mesoporous | | | 4 |
| ExMMZ-112C | Zeolite meso-$Al_2O_3$—Si | | | 5 |
| ExMMZ-113C | Zeolite meso-$Al_2O_3$—Si | | | 6 |
| ExMMZ-114C | Zeolite meso-$Al_2O_3$—Si | | | 7 |
| 15Ni-EAS | $Al_2O_3$—Si | 15 | — | 8 |
| 15Co-EAS | $Al_2O_3$—Si | — | 15 | 9 |
| 15Ni-EASMeso | $Al_2O_3$ mesoporous-Si | 15 | — | 10 |
| 15Ni-ExMMZ-112C | Zeolite meso-$Al_2O_3$—Si | 15 | — | 11 |
| 15Ni-ExMMZ-113C | Zeolite meso-$Al_2O_3$—Si | 15 | — | 12 |
| 15Ni-ExMMZ-114C | Zeolite meso-$Al_2O_3$—Si | 15 | — | 13 |
| CMA | Commercial reference catalyst alumina-Zeolite base | | | |

EXAMPLE 12. Preparation of the catalyst 15Ni-ExMMZ-113C. The impregnation solution was prepared dissolving 8.75 g of nickel nitrate $Ni(NO_3)_2 \cdot 6H_2O$ in 66 ml of water double-distilled with agitation. Once the nickel was dissolved the solution is turned transparent green. Afterwards, the solution is concentrated to a suitable volume to be used in the impregnation of 13.2 g of support ExMMZ-113C to fill in pores. The amount of dissolved salts varies based on the concentration of metals desired to be obtained in the final solid which was of 15% by weight of nickel, and the material was taken to a drying process at 120° C. for a period of 12 hours and then to a burning in air flow at a temperature of 400° C. for 4 hours. The catalyst was labelled as 15Ni-ExMMZ-113C.

EXAMPLE 13. Preparation of catalyst 15Ni-ExMMZ-114C. The impregnation solution was prepared dissolving 8.75 g od nickel nitrate $Ni(NO_3)_2 \cdot 6H_2O$ in 66 ml of water double-distilled water with stirring. Once the nickel was dissolved, the solution turned transparent green. Afterwards, the solution was concentrated to a suitable volume to be used in the impregnation of 13.2 g of support ExMMZ-114C to fill in pores. The amount of dissolved salts varies based on the concentration of metals desired to be obtained in the final solid which was of 15% by weight of nickel; the material was taken to a drying process at 120° C. for a period of 12 hours and then a burning in air flow at a temperature of 400° C. for 4 hours. The catalyst was labelled as 15Ni-ExMMZ-114C.

EXAMPLE 14. Thermal assessment of lignin Kraft at 60° C. with water/ethanol ratio (v/v) of 50/50. The thermal assessment was carried out at 60° C. in a batch-type reactor (Reactor Parr 4842) with a 250 ml capacity. The water/ethanol ratio (v/v) was 1.2 (50 mL water/50 mL ethanol). 2 g of lignin Kraft was used during reaction tests under a 4,137 kPa (600 psi) hydrogen pressure with mechanical stirring at 1000 rpm. Once said conditions were reached, the reaction is left for a period of 3 hours. The autogenous pressure reached was of 8,274 kPa (1200 psi).

When the reaction was completed, the reactor was disassembled from the heating systems to be immediately cooled.

The reaction product was treated under the following methodology:

1) Filter the reactor contents in a kitasato flask and filter paper (Whatman brand number 2, that is, for a medium filter).

2) The liquid reaction mixture (ethanol-water) was placed in a separation funnel. The organic phase contains the lignin depolymerisation products. The aqueous phase contains unreacted lignin.
3) Over the filtration funnel, 100 mL of dichloromethane (DCM) are added so as to wash the solids contained in the filter paper.
4) Afterwards the liquid mixture is poured in a separation funnel and the phases are separated (aqueous and organic).
5) Two further washes are carried out, using 50 mL DCM in the aqueous phase left over in the separation funnel, so as to complete the extraction of the organic phase.
6) The aqueous phase contained in the funnel is preserved for its further analysis in a gas chromatograph coupled to a mass spectrometry detector and library NIST/EPA/NIH Mass Spectral Search Library V2.0f (GC-MS, GC7820A-MSD 5975, Agilent Technologies).
7) On the other hand, the final organic phase is placed on a rotary evaporator. First it is heated at 40° C. at 50 rpm to separate DCM.
8) Afterwards, it is heated at 85° C. at 50 rpm and then in another container the ethanol contained in the sample is separated.
9) The liquid product of the final organic phase is placed in a flask for its further analysis in a GC-MS chromatograph.
10) The solid contained in the filter paper is placed in the over at 120° C., for a period of 24 h, and then it is weighted, to quantify the conversion by weight.
11) The lignin conversion was determined as follows: Xlignin=(Initial weight-Final weight)*100/Initial weight. The initial and final weight of lignin is dry base.

The lignin conversion was of 0.5% by weight. The reaction products, which are generated in greater amounts, are vanillin, aceto-vanillin and 4-hydroxy-3-methoxybenzeneacetic acid.

EXAMPLE 15. Thermal assessment of lignin Kraft at 80° C. with water/ethanol ratio (v/v) of 50/50. The thermal assessment was carried out at 80° C. in a batch-type reactor (Reactor Parr 4842) with a 250 ml capacity, under the same methodology as forth in Example 14. The lignin conversion was of 3.8% by weight. The reaction products generated in greater amounts are vanillin, aceto-vanillin and 4-hydroxi-3-methoxybenzeneacetic acid.

EXAMPLE 16. Thermal assessment of lignin Kraft at 140° C. with water/ethanol ratio (v/v) of 50/50. The thermal assessment was carried out at 140° C. in a batch-type reactor (Reactor Parr 4842) with a 250 mL capacity, under the same methodology as forth in Example 14. The lignin conversion was of 11.5% by weight. The reaction products generated in greater amounts are guaiacol, vanillin and aceto-guaiacona.

EXAMPLE 17. Thermal assessment of lignin Kraft at 220° C. with water/ethanol ratio (v/v) of 50/50. The thermal assessment was carried out at 220° C. in a batch-type reactor (Reactor Parr 4842) with a 250 mL capacity, under the same methodology as forth in Example 14. The lignin conversion was of 39.7% by weight. The reaction products generated in greater amounts are guaiacol, p-ethyl-guaiacol, p-propyl-guaiacol, aceto-guaiacol, homovanilic acid, vanillin, isoeugenol, creosol. FIG. 1 shows a chromatogram with products distribution and retention time.

EXAMPLE 18. Thermal assessment of lignin Kraft at 260° C. with water/ethanol ratio (v/v) of 50/50. The thermal assessment was carried out at 260° C. in a batch-type reactor (Reactor Parr 4842) with a 250 ml capacity, under the same methodology as forth in Example 14. The lignin conversion was of 53.4% by weight. The reaction products generated in greater amounts are the same as in Example 17. FIG. 1 shows a chromatogram with the products distribution and retention time.

EXAMPLE 19. Thermal assessment of lignin Kraft at 290° C. with water/ethanol ratio (v/v) of 50/50. The thermal assessment was carried out at 290° C. in a batch-type reactor (Reactor Parr 4842) with a 250 ml capacity, under the same methodology as forth in Example 14. The lignin conversion was of 59% by weight.

The activation energy calculated based on Examples 14, 15, 16, 17, 18 and 19 was of 7.05 kcal/mol (29.52 KJ/mol). The reaction products generated in greater amounts are the same as in Example 17. FIG. 1 shows a chromatogram with products distribution and retention time.

EXAMPLE 20. Thermal assessment at 290° C. of lignin Kraft with water/ethanol ratio (80/20). The thermal assessment was carried out at 290° C. in a batch-type reactor (Reactor Parr 4842) with a 250 ml capacity. The water/ethanol ratio (v/v) was 80/20. 2 g of lignin Kraft was used in the reaction test under a 4, 137 kPa (600 psi) hydrogen pressure with mechanical stirring at 1000 rpm. Once said conditions were reached the reaction is left for a period of 3 hours. When the reaction is completed, the reactor is dissembled from the heating system to be cooled immediately. The reaction product was treated under the same methodology used in Example 14. The lignin conversion was of 48% by weight. The reaction products generated in greater amounts are the same as in Example 17. FIG. 1 shows a chromatogram with products distribution and retention time.

EXAMPLE 21. Thermal assessment at 290° C. of lignin Kraft with water/ethanol ratio (20/80). The thermal assessment was carried out at 290° C. in a batch-type reactor (Reactor Parr 4842) with a 250 ml capacity. The water/ethanol ratio (v/v) was 20/80. 2 g of lignin Kraft was used in the reaction test under a 4, 137 kPa (600 psi) hydrogen pressure with mechanical stirring at 1000 rpm. Once said conditions were reached the reaction is left for a period of 3 hours. When the reaction is completed, the reactor is dissembled from the heating system to be cooled immediately. The reaction product was treated under the same methodology used in Example 14. In this case the lignin conversion was of 58% by weight, to the reaction timings. The reaction products generated in greater amounts are the same as in Example 17. FIG. 1 shows a chromatogram with products distribution and retention time.

EXAMPLE 22. Thermal assessment at 290° C. of lignin Kraft with water/ethanol ratio (50/50), 1 hour. The thermal assessment was carried out at 290° C. in a batch-type reactor (Reactor Parr 4842) with a 250 mL capacity. The water/ethanol ratio (v/v) was 50/50. 2 g of lignin Kraft was used in the reaction test under a 4, 137 kPa (600 psi) hydrogen pressure with mechanical stirring at 1000 rpm. Once said conditions were reached the reaction is left for a period of 1 hour. When the reaction is completed, the reactor is dissembled from the heating system to be cooled immediately. The reaction product was treated under the same methodology used in Example 14. The lignin conversion was of 57% by weight with a reaction time of 1 hour. The reaction products generated in greater amounts are the same as in Example 17. FIG. 1 shows a chromatogram with products distribution and retention time.

EXAMPLE 23. Thermal assessment at 290° C. of lignin Kraft with water/ethanol ratio (50/50), 6 hours. The thermal assessment was carried out at 290° C. in a batch-type reactor (Reactor Parr 4842) with a 250 ml capacity. The water/ethanol ratio (v/v) was 50/50. 2 g of lignin Kraft was used in the reaction test under a 4,137 kPa (600 psi) hydrogen pressure with mechanical stirring at 1000 rpm. Once said conditions were reached the reaction is left for a period of 6 hours. When the reaction is completed, the reactor is dissembled from the heating system to be cooled immediately. The reaction product was treated under the same methodology used in Example 14. The lignin conversion was of 57% by weight with a reaction time of 6 hours. The reaction products generated in greater amounts are the same as in Example 17. FIG. 1 shows a chromatogram with products distribution and retention time.

EXAMPLE 24. Thermal assessment at 290° C. of lignin Kraft with water/ethanol ratio (50/50), in basic medium. Conversion of lignin based on the reaction medium. The thermal assessment was carried out at 290° C. in a batch-type reactor (Reactor Parr 4842) with a 250 mL capacity. The water/ethanol ratio (v/v) was 60/50. Three hundred mg of NaOH was used as basic medium. 2 g of lignin Kfraft was used in the reaction test under a 4, 137 kPa (600 psi) hydrogen pressure with mechanical stirring at 1000 rpm. Once said conditions were reached the reaction is left for a period of 3 hours. When the reaction is completed, the reactor is dissembled from the heating system to be cooled immediately. The reaction product was treated under the same methodology used in Example 14. The lignin conversion was of 51.3% by weight in basic medium. The reaction products generated in greater amounts are the same as in Example 17.

FIG. 1 shows a chromatogram with products distribution and retention time.

TABLE 2

Thermal assessments with lignin Kraft.

| Temperature (° C.) | Ethanol:H$_2$O ratio (v/v) | Conversion (% weight) | Time (h) | Selectivity (%) | | Example # |
|---|---|---|---|---|---|---|
| | | | | Aromatic | Non-aromatic | |
| 60 | 50:50 | 0.50 | 3 | 100.00 | 0.00 | 14 |
| 80 | 50:50 | 3.80 | 3 | 100.00 | 0.00 | 15 |
| 140 | 50:50 | 11.5 | 3 | 95.08 | 4.92 | 16 |
| 220 | 50:50 | 39.7 | 3 | 98.42 | 1.42 | 17 |
| 260 | 50:50 | 53.4 | 3 | 60.21 | 39.79 | 18 |
| 290 | 50:50 | 59.0 | 3 | 55.30 | 44.70 | 19 |
| 290 | 80:20 | 48.0 | 3 | 56.54 | 43.46 | 20 |
| 290 | 20:80 | 58.0 | 3 | 37.87 | 62.13 | 21 |
| 290 | 20:80 | 57.0 | 1 | 51.50 | 48.50 | 22 |
| 290 | 50:50 | 67.0 | 6 | 78.90 | 20.18 | 23 |
| 290 | 50:50 | 51.3 | 3 (1) | 50.98 | 49.01 | 24 |
| 290 | 50:50 | 69.0 | 3 (2) | 31.53 | 68.47 | 25 |

(1) Basic medium (NaOH);
(2) Acid medium (HCl).

EXAMPLE 25. Thermal assessment at 290° C. of lignin Kraft with water/ethanol ratio (50/50), in acid medium. Conversion of lignin based on the reaction medium. The thermal assessment was carried out at 290° C. in a batch-type reactor (Reactor Parr 4842) with a 250 mL capacity. The water/ethanol ratio (v/v) was 50/50. For the acid medium, 300 mg of HCl was used. Two g of lignin Kfraft was used in the reaction test under a 4,137 kPa (600 psi) hydrogen pressure with mechanical stirring at 1000 rpm. Once said conditions were reached the reaction is left for a period of 3 hours. When the reaction is completed, the reactor is dissembled from the heating system to be cooled immediately. The reaction product was treated under the same methodology used in Example 14. The lignin conversion was of 69% by weight in acid medium; the reaction products generated in greater amounts are the same as in Example 17. FIG. 1 shows a chromatogram with products distribution and retention time.

EXAMPLE 26. Thermal assessment of sugar cane bagasse lignin (SCBL) at 260° C. The thermal assessment was carried out at 260° C. batch-type reactor (Reactor Parr 4842) with a 300 ml capacity. The water/ethanol ratio (v/v) was of 50/50. 10 g sugar cane bagasse lignin (SCBL) were used in a reaction test under an 7102 kPa (1030 psi) nitrogen pressure with mechanical stirring of 250 rpm. Once said conditions were reached, the reaction is left for a period of 1 hour. When the reaction was completed, the reactor is dissembled from the heating system to be cooled immediately. The reaction product was treated under the same methodology used in Example 14. The sugar cane bagasse lignin conversion was ≥90% mass base, wherein the selectivity was of 67.3% to aromatic products, 12.3% to furans and 20.4% to non-aromatic compounds.

EXAMPLE 27. Assessment of the EAS catalytic formulation with sugar cane bagasse lignin (SCBL). The catalytic assessment with the EAS catalyst prepared as set forth under Example 2, was carried out at 260° C. in a batch-like reactor (Reactor Parr 4842) with a 300 ml capacity. The water/ethanol ratio (v/v) was of 50/50. 10 g sugar cane bagasse lignin (SCBL) were used in a reaction test, the pressure was kept at 7102 kPa (1030 psi) nitrogen pressure with mechanical stirring of 250 rpm and 1 g of the EAS catalyst. Once said conditions were reached, the reaction is left for a period of 1 hour. When the reaction was completed, the reactor is dissembled from the heating system to be cooled immediately. The reaction product was treated under the same methodology used in Example 14. The IMP lignin conversion was ≥ 90% mass base, the selectivity was of 62.8% to aromatic products, 4.7% to furans and 32.4% to non-aromatic compounds.

EXAMPLE 28. Assessment of the 15Ni-EAS catalytic formulation with sugar cane bagasse lignin (SCBL). The thermal assessment was carried out at 260° C. in a batch-like reactor (Reactor Parr 4842) with a 300 mL capacity. The water/ethanol ratio (v/v) was of 50/50. 10 g sugar cane bagasse lignin (SCBL) were used in the reaction test under a 7102 kPa (1030 psi) nitrogen pressure with mechanical stirring of 250 rpm and 1 g of the 15Ni-EAS catalyst prepared according to the methodology described under Example 8. Once said conditions were reached, the reaction is left for a period of 1 hour. When the reaction was completed, the reactor is dissembled from the heating system to be cooled immediately. The reaction product was treated under the same methodology used in Example 17. The lignin IMP conversion was ≥ 90% mass base, the selectivity was of 49.6% to aromatic products, 6.2% to furans and 44.2% to non-aromatic compounds.

EXAMPLE 29. Assessment of the MMZ-112C catalytic formulation with sugar cane bagasse lignin (SCBL). The thermal assessment was carried out at 260° C. in a batch-like reactor (Reactor Parr 4842) with a 300 mL capacity. The water/ethanol ratio (v/v) was of 50/50. 10 g sugar cane bagasse lignin (SCBL) were used in the reaction test under a 7102 kPa (1030 psi) nitrogen pressure with mechanical stirring of 250 rpm and 1 g of the MMZ-112C catalyst prepared according to the methodology described under Example 4. Once said conditions were reached, the reaction is left for a period of 1 hour. When the reaction was completed, the reactor is dissembled from the heating system to be cooled immediately. The reaction product was treated under the same methodology used in Example 8. The sugar cane bagasse lignin conversion was >90% mass base, wherein the selectivity was of 67.6% to aromatic products, 6.1% to furans and 26.3% to non-aromatic compounds.

EXAMPLE 30. Assessment of the CMA catalytic formulation with sugar cane bagasse lignin (SCBL). The thermal assessment was carried out at 260° C. in a batch-like reactor (Reactor Parr 4842) with a 300 mL capacity. The water/ethanol ratio (v/v) was of 50/50. 10 g sugar cane bagasse lignin (SCBL) were used in the reaction test under a 7102 kPa (1030 psi) nitrogen pressure with mechanical stirring of 250 rpm and 1 g of the CMA catalyst (commercial reference catalyst alumina based) Table 1. Once said conditions were reached, the reaction is left for a period of 1 hour. When the reaction was completed, the reactor is dissembled from the heating system to be cooled immediately. The reaction product was treated under the same methodology used in Example 14. The sugar cane bagasse lignin (SCBL) conversion was >90% mass base, wherein the selectivity was of 47.64% to aromatic products, 5.3% to furans and 44.7% to non-aromatic compounds.

EXAMPLE 31. Thermal assessment with sugar cane bagasse (SCB) at 260° C. at 7102 kPa (1030 psi). The thermal assessment was carried out at 260° C. in a batch-like reactor (Reactor Parr 4842) with a 300 mL capacity. The water/ethanol ratio (v/v) was of 50/50. Twenty g sugar cane bagasse (SCB) were used in the reaction test under a 7102 kPa (1030 psi) nitrogen pressure with mechanical stirring of 250 rpm. Once said conditions were reached, the reaction is left for a period of 1 hour. When the reaction was completed, the reactor is dissembled from the heating system to be cooled immediately. The reaction product was treated under the same methodology used in Example 14. The sugar cane bagasse (SCB) conversion was >90% mass base, wherein the selectivity was of 39.1% to aromatic products, 13.9% to furans and 47.1% to non-aromatic compounds.

EXAMPLE 32. Thermal assessment with sugar cane bagasse (SCB) at 260° C. at 12,410 kPa (1800 psi). The thermal assessment was carried out at 260° C. in a batch-like reactor (Reactor Parr 4842) with a 300 mL capacity. The water/ethanol ratio (v/v) was of 60/50. 20 g sugar cane bagasse (SCB) were used in the reaction test under a 12,410 kPa (1800 psi) nitrogen pressure with mechanical stirring of 250 rpm. Once said conditions were reached, the reaction is left for a period of 1 hour. When the reaction was completed, the reactor is dissembled from the heating system to be cooled immediately. The reaction product was treated under the same methodology used in Example 14. The sugar cane bagasse (SCB) conversion was >90% mass base, wherein the selectivity was of 57.7% to aromatic products, 19.8% to furans and 23.4% to non-aromatic compounds.

EXAMPLE 33. Assessment of the 15Ni-EASMeso catalytic formulation from sugar cane bagasse (SCB). The thermal assessment was carried out at 260° C. in a batch-like reactor (Reactor Parr 4842) with a 300 ml capacity. The water/ethanol ratio (v/v) was of 50/50. 20 g sugar cane bagasse were used in the reaction test under a 7102 kPa (1030 psi) nitrogen pressure with mechanical stirring of 250 rpm and 1 g of the 15Ni-EASMeso catalyst prepared according to the methodology described under Example 10. Once said conditions were reached, the reaction is left for a period of 1 hour. When the reaction was completed, the reactor is dissembled from the heating system to be cooled immediately. The reaction product was treated under the same methodology used in Example 14. The sugar cane bagasse conversion was ≥90% mass base, wherein the selectivity was of 37.3% to aromatic products, 22% to furans and 40.6% to non-aromatic compounds.

TABLE 3

Assessments with SCBL y SCB.

| Catalyst | Lignin | Weight (g) | Pressure (kPa) | Selectivity (%) Aromatic | Furans | Non-aromatic | Example # |
|---|---|---|---|---|---|---|---|
| Thermal | LBC | 10 | 7102 | 67.3 | 12.3 | 20.4 | 26 |
| EAS | LBC | 10 | 7102 | 62.8 | 4.7 | 32.4 | 27 |
| 15Ni-EAS | LBC | 10 | 7102 | 49.6 | 6.2 | 44.2 | 28 |
| MMZ-112C | LBC | 10 | 7102 | 67.6 | 6.1 | 26.3 | 29 |
| CMA | LBC | 10 | 7102 | 47.64 | 5.3 | 44.7 | 30 |
| Thermal | BC | 20 | 7102 | 39.1 | 13.9 | 47.1 | 31 |
| Thermal | BC | 20 | 7102 | 57.7 | 19.8 | 23.4 | 32 |
| 15Ni-EASMeso | BC | 20 | 7102 | 37.3 | 22 | 40.6 | 33 |
| MMZ-112C | BC | 20 | 7102 | 52.7 | 27 | 20.3 | 34 |

Conversion: ≥90% by weight; Temperature: 260° C.; Ethanol:$H_2O$ ratio (v/v):60:50; Catalyst's weight: 1 g; SCBL: Sugar cane bagasse lignin; SCB: Sugar cane bagasse.

EXAMPLE 34. Assessment of the MMZ-112C catalytic formulation from sugar cane bagasse (SCB). The thermal assessment was carried out at 260° C. in a batch-like reactor (Reactor Parr 4842) with a 300 mL capacity. The water/ethanol ratio (v/v) was of 50/50. 20 g sugar cane bagasse were used in the reaction test under a 7102 kPa (1030 psi) nitrogen pressure with mechanical stirring of 250 rpm and 1 g of the MMZ-112C catalyst prepared according to the methodology described under Example 4. Once said conditions were reached, the reaction is left for a period of 1 hour. When the reaction was completed, the reactor is dissembled from the heating system to be cooled immediately. The reaction product was treated under the same methodology used in Example 14. The sugar cane bagasse conversion was ≥ 90% mass base, wherein the selectivity was of 52.7% to aromatic products, 27% to furans and 20.3% to non-aromatic compounds.

EXAMPLES 35, 36 and 37. Assessment in sodium lignosulfonate depolymerisation in a pilot micro-plant with 15Ni-EAS catalyst. A sodium lignosulfonate depolymerisation catalytic assessment was carried out in a pilot micro-plant system equipped with a fixed bed tubular reactor operating in ascending flow. 7.5 mL of granulated catalyst (15Ni-EAS, mesh EE.UU. 16-20, about 1 mm average particle size, prepared according to the methodology described under Example 8) were loaded diluted with an equivalent volume of SiC EE.UU. mesh 60 (about 0.25 mm diameter). Before the assays, the catalyst was subjected to a reduction process consisting in passing $H_2$ flow (5 L/h), at 70 kg/cm$^2$ and 350° C. Once the catalyst was active (1 hour) the system was taken to the lignin depolymerisation assessment conditions ($N_2$ flow of 5 L/h, 70 kg/cm$^2$ and T=260° C.) feeding sodium lignosulfonate (2 g in 100 mL ethanol/water mixture, 50/50 vol/vol) at a speed such that allows carrying out the assessment at LHSV 5, 3, and 2 h-1. The liquid products obtained from the reaction showed a transparent yellow colour. The liquid products obtained from the reaction showed a transparent yellow colour. The separation of the organic fraction was carried out by adding dichloromethane following the same procedure as described under Example 8. The aqueous fraction resulted totally transparent, indicating the absence of dissolved lignin therein and that the depolymerisation was of 100%. The product selectivity results were grouped as oxygenated and deoxygenated aromatic, paraffin, olefin, isoparaffin and naphthenes, alcohols and ketones, and ethers and esters. The results are shown in Table 4, and it can be appreciated that an LHSV at 3 h-1 the selectivity of aromatic hydrocarbons was of 52% of which 26% correspond to deoxygenated aromatic and the 26% leftover corresponds to oxygenated aromatic, which indicates that the catalyst 15Ni-EAS carries out the deoxygenation of the oxygenated aromatics produced during lignin depolymerisation. Moreover, a noticeable selectivity to paraffin and isoparaffin, olefin and naphthenes is observed, indicating that an opening of the aromatic rings is carried out. The results of the products selectivity are shown in Table 4.

TABLE 4

Sodium lignosulfonate depolymerisation with 15Ni-EAS catalyst.
Effect of LHSV (liquid hourly space velocity).

| | Selectivity (%) | | | | | | | | |
|---|---|---|---|---|---|---|---|---|---|
| LHSV ($h^{-1}$) | Arom. no oxi. | Arom. oxi. | Alcohols | Hisopara. | Paraffin | Naphthenes | Others | No id. | Example. |
| 5 | 6.53 | 28.84 | 3.70 | 2.46 | 22.10 | 0.24 | 3.79 | 32.34 | 35 |
| 3 | 26.00 | 26.00 | 1.26 | 2.98 | 9.81 | 2.24 | 9.8 | 21.91 | 36 |
| 2 | 25.80 | 4.42 | 0.0 | 6.50 | 16.57 | 0.46 | 1.73 | 44.52 | 37 |

Temperature: 260° C.; Ethanol:$H_2O$ ratio (v/v) 50:50; Catalyst volume: 7.5 ml; $N_2$ Pressure: 70 Kg/cm$_2$.

EXAMPLES 38, 39 and 40. Assessment in sodium lignosulfonate depolymerisation in a pilot micro-plant with 15Co-EAS catalyst. A sodium lignosulfonate (pre-treated) depolymerisation catalytic assessment was carried out in a pilot micro-plant system equipped with a fixed bed tubular reactor operating in ascending flow. 7.5 mL of granulated catalyst (15Co-EAS, prepared according to the methodology described under Example 9, mesh EE.UU. 16-20, about 1 mm average particle size). Before the activity assessment assays, the catalyst material was reduced in $H_2$ flow (5 L/h), at 70 kg/cm$^2$ and 350° C. Once the catalyst was active (1 hour) the system was taken to the lignin depolymerisation assessment conditions ($N_2$ flow of 5 L/h, 70 kg/cm$^2$ and T=260° C.) feeding pre-treated sodium lignosulfonate (2 g in 100 mL ethanol/water mixture, 50/50 vol/vol). During pre-treatment, a mixture of 6 g lignin+150 mL $H_2O$+150 mL ethanol was subjected for 1 hour at 260° C., an initial pressure of $N_2$ at 70 kg/cm$^2$. Speed spaces were used in the interval of 2 to 5 h-1. The product selectivity results are shown in Table 5.

operating in ascending flow. 7.5 mL of the catalyst prepared according to the methodology described under Example 2, granulated (EAS, mesh EE.UU. 16-20, about 1 mm average particle size) were loaded. Before the activity assessment assays, the catalytic material was reduced in $H_2$ flow (5 L/h), at 70 kg/cm$^2$ and 350° C. Once the catalyst was active (1 hour) the system was taken to the lignin depolymerisation assessment conditions ($N_2$ flow of 5 L/h, 70 kg/cm$^2$ and T=260° C.) feeding sodium lignosulfonate (pre-treated) (2 g in 100 mL ethanol/water mixture, 50/50 vol/vol). During the pre-treatment, a mixture of 6 g lignin+150 mL $H_2O$+150 ethanol was subjected for 1 hour at 260° C., at $N_2$ initial pressure of 70 kg/cm$^2$.

Speed spaces in the interval of 2 to 5 h-1 were used. The results of the aromatic products selectivity are shown in Table 6.

EXAMPLES 44, 45 and 46. Assessment in sugar cane bagasse (SCB) lignin depolymerisation in pilot micro-plant. A sugar cane bagasse lignin thermal depolymerisation assessment was carried out in a pilot micro-plant system equipped with a fixed bed tubular reactor operating in ascending flow. 7.5 mL of the granulated catalyst (15Ni-EAS prepared according to the methodology described under Example 8, mesh EE.UU. 16-20, about 1 mm average particle size) were loaded. Before the activity assessment assays, the catalytic material was reduced in $H_2$ flow (5 L/h), at 70 kg/cm$^2$ and 350° C. Once the catalyst was active (1 hour) the system was taken to the lignin depolymerisation assessment conditions ($N_2$ flow of 5 L/h, 70 kg/cm$^2$ and T=260° C.) feeding pre-treated sugar cane bagasse lignin (3.3 g in 100 ml ethanol/water mixture, 50/50 vol/vol).

TABLE 5

Sodium lignosulfonate depolymerisation with 15Co-EAS catalyst. Effect of LHSV.

| | Selectivity (%) | | | | | | | |
|---|---|---|---|---|---|---|---|---|
| LHSV ($h^{-1}$) | Arom. no oxi. | Arom. oxi. | Alcohols | Olef.-Isoparaf.-Paraffin | Ether-Ester | Naphthenes-furans | Others | No id. | Ex-ample |
| 5 | 12.86 | 38.61 | 12.04 | 5.40 | 4.27 | 1.87 | 0.09 | 24.86 | 38 |
| 3 | 0.59 | 56.30 | 15.97 | 1.46 | 0.38 | 3.24 | 0.02 | 22.04 | 39 |
| 2 | 5.21 | 39.50 | 14.29 | 11.96 | 2.42 | 3.39 | 3.07 | 20.16 | 40 |

Temperature: 260° C.; Ethanol:$H_2O$ ratio (v/v) 50:50; Catalyst volume: 7.5 ml; $N_2$ Pressure: 70 Kg/cm$^2$.

EXAMPLES 41, 42 and 43. Assessment in sodium lignosulfonate depolymerisation in a pilot micro-plant with EAS catalyst. A sodium lignosulfonate (pre-treated) depolymerisation catalytic assessment was carried out in a pilot micro-plant system equipped with a fixed bed tubular reactor During the pre-treatment, a mixture of 10 g lignin+150 mL $H_2O$+150 ethanol was subjected for 1 hour at 260° C., at $N_2$ initial pressure of 70 kg/cm$^2$.

Speed spaces in the interval of 2 to 5 h-1 were used. The results of the aromatic products selectivity are shown in Table 7.

TABLE 6

Catalytic assessment of sodium lignosulfonate
with EAS catalyst. Effect of LHSV.

| | | | | Selectivity (%) | | | | | |
|---|---|---|---|---|---|---|---|---|---|
| LHSV (h$^{-1}$) | Arom. no oxi. | Arom. oxi | Alcohols | Olef.-Isoparaf.-Paraffin | Ether-Ester | Naphthenes-furans | Others | No id. | Example |
| 5 | 1.08 | 40.83 | 7.33 | 0 | 2.35 | 3.05 | 0.72 | 44.64 | 41 |
| 3 | 1.08 | 40.70 | 7.64 | 0 | 2.35 | 2.88 | 0.71 | 44.64 | 42 |
| 2 | 2.45 | 56.38 | 17.34 | 0 | 0.95 | 4.79 | 0.01 | 18.08 | 43 |

Temperature: 260° C.; Ethanol:H$_2$O ratio (v/v) 50:50; Catalyst volume: 7.5 ml; N$_2$ Pressure: 70 Kg/cm$^2$.

EXAMPLES 47, 48, 49 and 50. Assessment of depolymerisation of black liqueur lignin from paper industry in pilot micro-plant. A depolymerisation catalytic assessment was carried out with black liqueur lignin, a paper industry residue, in a pilot micro-plant system with a fixed bed tubular reactor operating in ascending flow. 7.5 mL of SiC EE.UU. mesh 60 (about 0.25 mm diameter) were loaded. The system was taken to lignin depolymerisation assessment conditions (N$_2$ flow of 5 L/h, 70 kg/cm$^2$ and T=260° C.) feeding black liqueur lignin (3.33 g in 100 mL ethanol/water mixture, 50/50 vol/vol). Speed spaces in the interval of 2 to 5 h-1 were used. The results of the aromatic products selectivity are shown in Table 8.

TABLE 7

Assessment of sugar cane bagasse lignin (SCBL) depolymerisation
with 15Ni-EAS catalyst. Effect of LHSV.

| | | | | Selectivity (%) | | | | | |
|---|---|---|---|---|---|---|---|---|---|
| LHSV (h$^{-1}$) | Arom. no oxi. | Arom. oxi | Alcohols | Olef-Isoparaf.-Paraffin | Ether-Ester | Naphthenes-furans | Others | No id. | Example. |
| 5 | 0.38 | 48.17 | 1.34 | 0.92 | 10.30 | 10.33 | 1.82 | 26.74 | 44 |
| 3 | 18.16 | 41.05 | 5.79 | 2.04 | 3.42 | 7.60 | 0.94 | 21.00 | 45 |
| 2 | 3.43 | 61.65 | 1.97 | 0 | 2.43 | 14.97 | 0.98 | 14.57 | 46 |

Temperature: 260° C.; Ethanol:H$_2$O ratio (v/v) 50:50; Catalyst volume: 7.5 ml; N$_2$ Pressure 70 Kg/cm$_2$.

EXAMPLES 51, 52 and 53. Catalytic assessment of sodium lignosulfonate depolymerisation in pilot micro-plant at different hydrogen pressures. A catalytic assessment of (pre-treated) sodium lignosulfonate depolymerisation was carried out in a pilot micro-plant system equipped with a fixed bed tubular reactor in ascending flow. 7.5 mL of SiC EE.UU. mesh 60 (about 0.25 mm diameter) were loaded at the bottom of the reactor, and then an equivalent volume of granulated catalyst (15Ni-EAS prepared according to the methodology under Example 8, mesh EE.UU. 16-20, about 1 mm average particle size) was added. Before the activity assessment assays, the catalytic material was reduced in H$_2$ flow (5 L/h), at 70 kg/cm$^2$ and 350° C. Once the catalyst was active (1 hour) the system was taken to the lignin depolymerisation assessment conditions (N$_2$ flow of 5 L/h, 70 kg/cm$^2$ and T=260° C.) feeding pre-treated sodium lignosulfonate lignin (2 g in 100 mL ethanol/water mixture, 50/50 vol/vol). During the pre-treatment, a mixture of 6 g lignin+ 150 mL H$_2$O+150 ethanol was subjected for 1 hour at 260° C., at N$_2$ initial pressure of 70 kg/cm$^2$. The hydrogen partial pressure effect was studied in the interval of 30 to 70 Kg/cm$^2$. The results of the aromatic products selectivity are shown in Table 9.

TABLE 8

Thermal assessment of black liqueur lignin from paper industry. Effect of LHSV.

| LHSV ($h^{-1}$) | Selectivity (%) | | | | | | | | |
|---|---|---|---|---|---|---|---|---|---|
| | Arom. no oxi | Arom. oxi. | Alcohols | Olef.-Isoparaf.-Paraffin | Ether-Ester | Naphthenes-furans | Nitrog. | No id. | Example. |
| 5 | 36.2 | 44.57 | 0.92 | 12.09 | 0 | 1.75 | 0 | 4.47 | 47 |
| 3 | 5.05 | 86.19 | 1.06 | 3.67 | 0 | 0 | 0 | 4.03 | 48 |
| 2 | 0 | 91.46 | 1.12 | 0 | 0 | 2.96 | 0 | 4.45 | 49 |
| 1 | 0 | 92.45 | 0 | 0 | 0 | 0 | 3 | 4.54 | 50 |

Temperature: 260° C.; Ethanol:$H_2O$ ratio (v/v) 50:50; SiC volume: 7.5 ml; $N_2$ Pressure: 70 Kg/$cm^2$

TABLE 9

Assessment of pre-treated sodium lignosulfonate depolymerisation with 15Ni-EAS catalyst. Effect of $H_2$ Pressure

| P (Kg/$cm^2$) | Selectivity (%) | | | | | | | | |
|---|---|---|---|---|---|---|---|---|---|
| | Arom. no oxi. | Arom. oxi. | Alcohols | Isoparaf. | Paraffin | Naphthenes | Others | No id. | Example. |
| 30 | 0 | 67.53 | 13.73 | 0 | 7.33 | 1.06 | 4.96 | 5.39 | 51 |
| 50 | 0 | 71.00 | 13.76 | 0 | 3.99 | 0 | 2.2 | 9.05 | 52 |
| 70 | 0 | 70.08 | 17.42 | 0 | 5.79 | 0 | 0 | 6.71 | 53 |

Temperature: 260° C.; Ethanol:$H_2O$ ratio (v/v) 50:50; Catalyst volume: 7.5 ml; LHSV: 3 $h^{-1}$.

The invention claimed is:

1. A catalytic composition for use in a process of lignin depolymerization and deoxygenation for obtaining aromatic hydrocarbons, comprising:
    a non-noble element of Group VIIIB of the periodic table, the non-noble element supported in a support material, wherein the support material comprises an inorganic oxide, the inorganic oxide selected from a mesoporous alumina modified by a second inorganic oxide, the second inorganic oxide selected from silicon dioxide to weaken the metal-support interaction, and wherein the material is mixed with a third silico aluminate component with a mesoporous zeolitic structure.

2. A process of lignin depolymerization and deoxygenation for obtaining aromatic hydrocarbons, comprising the steps of:
    dissolving a lignin in a mixture of protic solvents placed in a container, creating a dissolved protic lignin mixture, and sealing the container;
    reacting the dissolved protic lignin mixture in one of a batch reaction system and a continuous flow reaction system at either an inert or reducing atmosphere;
    stirring the dissolved protic lignin mixture; and
    applying pressure with one of an inert gas and hydrogen pressure to the reaction system to maintain a set of determined reaction conditions for a determined reaction time;
    wherein the reaction conditions include a determined reaction temperature of between 40° C. to 320° C., inclusive, and a determined operation pressure of from 5 kg/$cm^2$ to 100 kg/$cm^2$, inclusive; and
    the process is carried out using a catalytic composition according to claim 1.

3. The process of claim 2, wherein the support material has an area between 200 $m^2$/g and 500 $m^2$/g, inclusive, an average pore diameter from 8 nm to 30 nm, inclusive, and pore volume from 0.5 cc/g to 2.0 cc/g, inclusive.

4. The process of claim 2, wherein the composition further comprises a non-modified mesoporous alumina mixed with an aluminum oxyhydroxide in boehmite phase.

5. The catalytic composition of claim 1, wherein the non-noble element from Group VIIIB of the periodic table is selected from a group consisting of Fe, Co, and Ni.

6. The catalytic composition of claim 1, wherein the support material has an area between 200 $m^2$/g and 500 $m^2$/g, inclusive, an average pore diameter from 8 nm to 30 nm, inclusive, and pore volume from 0.5 cc/g to 2.0 cc/g, inclusive.

7. The catalytic composition of claim 1, further comprising a non-modified mesoporous alumina mixed with an aluminum oxyhydroxide in boehmite phase.

8. The process of claim 2, wherein the non-noble element from Group VIIIB of the periodic table is selected from a group consisting of Fe, Co, and Ni.

9. A catalytic composition for use in a process of lignin depolymerization and deoxygenation for obtaining aromatic hydrocarbons, comprising:
    a non-noble element of Group VIIIB of the periodic table, the non-noble element supported in a support material, wherein the support material comprises between 10% to 70%, inclusive, mesoporous alumina, 10% to 70%, inclusive, mesoporous zeolite, and 10% to 70%, inclusive, aluminum oxyhydroxide in boehmite phase.

10. The catalytic composition of claim 9, wherein the support material comprises between 30% to 70%, inclusive, mesoporous alumina and 30% to 70%, inclusive, aluminum oxyhydroxide in boehmite phase.

11. A process of lignin depolymerization and deoxygenation for obtaining aromatic hydrocarbons, comprising the steps of:
    dissolving a lignin in a mixture of protic solvents placed in a container, creating a dissolved protic lignin mixture, and sealing the container;

reacting the dissolved protic lignin mixture in one of a batch reaction system and a continuous flow reaction system at either an inert or reducing atmosphere;

stirring the dissolved protic lignin mixture; and applying pressure with one of an inert gas and hydrogen pressure to the reaction system to maintain a set of determined reaction conditions for a determined reaction time;

wherein the reaction conditions include a determined reaction temperature of between 40° C. to 320° C., inclusive, and a determined operation pressure of from 5 kg/cm$^2$ to 100 kg/cm$^2$, inclusive; and the process is carried out using a catalytic composition according to claim 9.

12. The process of claim 11, wherein the support material comprises between 30% to 70%, inclusive, mesoporous alumina and 30% to 70%, inclusive, aluminum oxyhydroxide in boehmite phase.

* * * * *